US011090338B2

(12) United States Patent
Barere et al.

(10) Patent No.: US 11,090,338 B2
(45) Date of Patent: Aug. 17, 2021

(54) METHODS FOR IMPROVED TREATMENT OF ADIPOSE TISSUE

(71) Applicant: Lifecell Corporation, Branchburg, NJ (US)

(72) Inventors: Aaron Barere, Hoboken, NJ (US); Jerome Connor, Doylestown, PA (US)

(73) Assignee: LifeCell Corporation, Madison, NJ (US)

( * ) Notice: Subject to any disclaimer, the term of this patent is extended or adjusted under 35 U.S.C. 154(b) by 69 days.

(21) Appl. No.: 13/929,252

(22) Filed: Jun. 27, 2013

(65) Prior Publication Data

US 2014/0017206 A1 Jan. 16, 2014

Related U.S. Application Data

(60) Provisional application No. 61/671,443, filed on Jul. 13, 2012.

(51) Int. Cl.
A61K 35/35 (2015.01)
A61L 27/36 (2006.01)

(52) U.S. Cl.
CPC .......... A61K 35/35 (2013.01); A61L 27/3604 (2013.01); A61L 27/3687 (2013.01); A61L 2430/34 (2013.01); A61L 2430/40 (2013.01)

(58) Field of Classification Search
None
See application file for complete search history.

(56) References Cited

U.S. PATENT DOCUMENTS

| 4,233,969 | A | 11/1980 | Lock et al. |
| 4,373,519 | A | 2/1983 | Errede et al. |
| 4,569,348 | A | 2/1986 | Hasslinger |
| 4,582,640 | A | 4/1986 | Smestad et al. |
| 4,681,571 | A | 7/1987 | Nehring |
| 4,703,108 | A | 10/1987 | Silver et al. |
| 4,753,634 | A | 6/1988 | Johnson |
| 4,902,508 | A | 2/1990 | Badylak et al. |
| 4,950,483 | A | 8/1990 | Ksander et al. |
| 4,969,912 | A | 11/1990 | Kelman et al. |
| 5,104,957 | A | 4/1992 | Kelman et al. |
| 5,131,850 | A | 7/1992 | Brockbank |
| 5,149,331 | A | 9/1992 | Ferdman et al. |
| 5,160,313 | A | 11/1992 | Carpenter et al. |
| 5,231,169 | A | 7/1993 | Constantz et al. |
| 5,254,133 | A | 10/1993 | Seid |
| 5,263,971 | A | 11/1993 | Hirshowitz et al. |
| 5,275,826 | A | 1/1994 | Badylak et al. |
| 5,284,655 | A | 2/1994 | Bogdansky et al. |
| 5,298,015 | A | 3/1994 | Komatsuzaki et al. |
| 5,332,802 | A | 7/1994 | Kelman et al. |
| 5,332,804 | A | 7/1994 | Florkiewicz et al. |
| 5,336,616 | A | 8/1994 | Livesey et al. |
| 5,364,756 | A | 11/1994 | Livesey et al. |
| 5,437,651 | A | 8/1995 | Todd et al. |
| 5,489,304 | A | 2/1996 | Orgill et al. |
| 5,549,584 | A | 8/1996 | Gross |
| 5,613,982 | A | 3/1997 | Goldstein |
| 5,632,778 | A | 5/1997 | Goldstein |
| 5,636,643 | A | 6/1997 | Argenta et al. |
| 5,641,518 | A | 6/1997 | Badylak et al. |
| 5,645,081 | A | 7/1997 | Argenta et al. |
| 5,681,561 | A * | 10/1997 | Hirshowitz et al. ......... 424/93.7 |
| 5,728,752 | A | 3/1998 | Scopelianos et al. |
| 5,739,176 | A | 4/1998 | Dunn et al. |
| 5,785,640 | A | 7/1998 | Kresch et al. |
| 5,800,537 | A | 9/1998 | Bell |
| D401,336 | S | 11/1998 | Muller et al. |
| 5,893,888 | A | 4/1999 | Bell |
| 5,901,717 | A | 5/1999 | Dunn et al. |
| 5,993,844 | A | 11/1999 | Abraham et al. |
| 6,027,743 | A | 2/2000 | Khouri et al. |
| D424,194 | S | 5/2000 | Holdaway et al. |
| 6,071,267 | A | 6/2000 | Zamierowski |
| 6,071,747 | A * | 6/2000 | Strosberg et al. ............ 435/467 |
| 6,096,347 | A | 8/2000 | Geddes et al. |
| 6,113,623 | A | 9/2000 | Sgro |
| 6,135,116 | A | 10/2000 | Vogel et al. |
| 6,179,872 | B1 | 1/2001 | Bell et al. |
| 6,194,136 | B1 | 2/2001 | Livesey et al. |
| 6,258,054 | B1 | 7/2001 | Mozsary et al. |
| 6,326,018 | B1 | 12/2001 | Gertzman et al. |
| 6,345,623 | B1 | 2/2002 | Heaton et al. |

(Continued)

FOREIGN PATENT DOCUMENTS

WO WO-1990/000060 A1 1/1990
WO WO-1996/040172 A1 12/1996

(Continued)

OTHER PUBLICATIONS

Smith et al., Plastic and Reconstructive Surgery, May 2006, vol. 117, No. 6, pp. 1836-1844.*
Kurita et al., Plastic and Reconstructive Surgery, Mar. 2008, vol. 121, No. 3, pp. 1033-1041.*
Ahn et al., "The past, present, and future of xenotransplantation" *Yonsei Med J.*, 45(6):1017-1024 (Dec. 31, 2004).
Allman et al., "Xenogeneic Extracellular Matrix Grafts Elicit a TH2-Restricted Immune Response" *Transplantation*, 71(11):1631-1640 (Jun. 15, 2001).

(Continued)

*Primary Examiner* — Scott Long
*Assistant Examiner* — Evelyn Y Pyla
(74) *Attorney, Agent, or Firm* — McCarter & English, LLP

(57) ABSTRACT

The present disclosure relates generally to methods of treatment of tissue prior to implantation. In one aspect, the methods of treatment include washing adipose tissue with detergents to improve the viability of adipose cells for implantation and/or to increase the amount of viable adipose cells per volume of tissue for implantation.

15 Claims, No Drawings

(56) References Cited

U.S. PATENT DOCUMENTS

| | | |
|---|---|---|
| 6,371,992 B1 | 4/2002 | Tanagho et al. |
| 6,432,710 B1 | 8/2002 | Boss, Jr. et al. |
| 6,485,723 B1 | 11/2002 | Badylak et al. |
| 6,553,998 B2 | 4/2003 | Heaton et al. |
| 6,576,265 B1 | 6/2003 | Spievack |
| 6,666,892 B2 | 12/2003 | Hiles et al. |
| 6,733,537 B1 | 5/2004 | Fields et al. |
| D492,995 S | 7/2004 | Rue et al. |
| 6,814,079 B2 | 11/2004 | Heaton et al. |
| 6,840,960 B2 | 1/2005 | Bubb |
| 6,933,326 B1 | 8/2005 | Griffey et al. |
| 7,070,584 B2 | 7/2006 | Johnson et al. |
| 7,198,046 B1 | 4/2007 | Argenta et al. |
| 7,358,284 B2 | 4/2008 | Griffey et al. |
| D575,393 S | 8/2008 | Stephens |
| 7,425,322 B2 | 9/2008 | Cohn et al. |
| 7,498,040 B2 | 3/2009 | Masinaei et al. |
| 7,498,041 B2 | 3/2009 | Masinaei et al. |
| 7,588,732 B2 | 9/2009 | Buss |
| 7,651,684 B2 | 1/2010 | Hedrick et al. |
| 7,700,819 B2 | 4/2010 | Ambrosio et al. |
| 7,763,769 B2 | 7/2010 | Johnson et al. |
| 7,780,649 B2 | 8/2010 | Shippert |
| 7,789,872 B2 | 9/2010 | Shippert |
| 7,794,449 B2 | 9/2010 | Shippert |
| 7,799,767 B2 | 9/2010 | Lamberti et al. |
| 7,838,021 B2 | 11/2010 | Lafont et al. |
| 8,062,286 B2 | 11/2011 | Shippert |
| 8,067,149 B2 | 11/2011 | Livesey et al. |
| 8,100,874 B1 | 1/2012 | Jordan et al. |
| 8,110,216 B2 | 2/2012 | Ambrosio et al. |
| 8,152,783 B2 | 4/2012 | Swain |
| 8,163,974 B2 | 4/2012 | Ambrosio et al. |
| 8,197,551 B2 | 6/2012 | Swain et al. |
| 8,197,806 B2 | 6/2012 | Girouard et al. |
| 8,257,372 B2 | 9/2012 | Swain et al. |
| 8,267,918 B2 | 9/2012 | Johnson et al. |
| 8,293,532 B2 | 10/2012 | Moynahan |
| 8,324,449 B2 | 12/2012 | McQuillan et al. |
| 8,333,740 B2 | 12/2012 | Shippert |
| D679,011 S | 3/2013 | Kitayama et al. |
| 8,409,860 B2 | 4/2013 | Moynahan |
| D683,851 S | 6/2013 | Greenhalgh |
| D687,549 S | 8/2013 | Johnson et al. |
| 8,512,695 B2 | 8/2013 | Austen, Jr. |
| D692,559 S | 10/2013 | Scheibel et al. |
| 8,622,997 B2 | 1/2014 | Shippert |
| 8,632,498 B2 | 1/2014 | Rimsa et al. |
| 2002/0103542 A1 | 8/2002 | Bilbo |
| 2002/0120185 A1 | 8/2002 | Johnson |
| 2002/0188280 A1 | 12/2002 | Nguyen et al. |
| 2003/0035843 A1 | 2/2003 | Livesey et al. |
| 2003/0143207 A1 | 7/2003 | Livesey et al. |
| 2003/0162707 A1* | 8/2003 | Fraser et al. ............ 514/12 |
| 2003/0225347 A1 | 12/2003 | Argenta et al. |
| 2004/0005246 A1 | 1/2004 | Efthimiadis et al. |
| 2004/0037735 A1 | 2/2004 | DePaula et al. |
| 2005/0028228 A1 | 2/2005 | McQuillan et al. |
| 2005/0043179 A1 | 2/2005 | Schmidt et al. |
| 2005/0084961 A1 | 4/2005 | Hedrick et al. |
| 2005/0159822 A1 | 7/2005 | Griffey et al. |
| 2006/0073592 A1 | 4/2006 | Sun et al. |
| 2006/0127375 A1 | 6/2006 | Livesey et al. |
| 2006/0153816 A1 | 7/2006 | Brown et al. |
| 2006/0184119 A1 | 8/2006 | Remde et al. |
| 2006/0210960 A1 | 9/2006 | Livesey et al. |
| 2006/0224144 A1 | 10/2006 | Lee |
| 2007/0078522 A2 | 4/2007 | Griffey et al. |
| 2007/0104759 A1 | 5/2007 | Dunn et al. |
| 2007/0106208 A1 | 5/2007 | Uber et al. |
| 2007/0219471 A1 | 9/2007 | Johnson et al. |
| 2007/0248575 A1 | 10/2007 | Connor et al. |
| 2008/0027542 A1 | 1/2008 | McQuillan et al. |
| 2008/0027562 A1 | 1/2008 | Fujisato et al. |
| 2008/0114277 A1 | 5/2008 | Ambrosio et al. |
| 2009/0035289 A1 | 2/2009 | Wagner et al. |
| 2009/0157017 A1 | 6/2009 | Ambrosio |
| 2009/0181104 A1 | 7/2009 | Rigotti et al. |
| 2009/0198167 A1 | 8/2009 | Ambrosio |
| 2009/0220579 A1 | 9/2009 | Hassingboe et al. |
| 2009/0287181 A1 | 11/2009 | Kagan et al. |
| 2009/0287190 A1 | 11/2009 | Shippert |
| 2009/0299328 A1 | 12/2009 | Mudd et al. |
| 2009/0306790 A1 | 12/2009 | Sun |
| 2009/0326515 A1 | 12/2009 | Kagan et al. |
| 2010/0021961 A1 | 1/2010 | Fujisato et al. |
| 2010/0040687 A1 | 2/2010 | Pedrozo et al. |
| 2010/0104542 A1 | 4/2010 | Austen, Jr. |
| 2010/0168689 A1 | 7/2010 | Swain et al. |
| 2010/0168720 A1 | 7/2010 | Swain et al. |
| 2010/0168870 A1 | 7/2010 | Swain et al. |
| 2010/0174162 A1 | 7/2010 | Gough et al. |
| 2010/0179515 A1 | 7/2010 | Swain et al. |
| 2010/0209408 A1 | 8/2010 | Stephen et al. |
| 2010/0268189 A1 | 10/2010 | Byrnes et al. |
| 2010/0272782 A1 | 10/2010 | Owens et al. |
| 2011/0009822 A1 | 1/2011 | Nielsen |
| 2011/0020271 A1 | 1/2011 | Niklason et al. |
| 2011/0152196 A1 | 6/2011 | Shah et al. |
| 2011/0184357 A1 | 7/2011 | Robinson et al. |
| 2011/0198353 A1 | 8/2011 | Tsao |
| 2011/0251566 A1 | 10/2011 | Zimnitsky et al. |
| 2012/0010728 A1 | 1/2012 | Sun et al. |
| 2012/0040013 A1 | 2/2012 | Owens et al. |
| 2012/0189588 A1 | 7/2012 | Nahas et al. |
| 2012/0263763 A1 | 10/2012 | Sun et al. |
| 2013/0053960 A1 | 2/2013 | Park et al. |
| 2013/0121970 A1 | 5/2013 | Owens et al. |
| 2013/0131635 A1 | 5/2013 | Rimsa et al. |
| 2013/0150825 A1 | 6/2013 | Rimsa et al. |
| 2013/0158515 A1 | 6/2013 | Austen, Jr. |
| 2013/0158676 A1 | 6/2013 | Hayzlett et al. |

FOREIGN PATENT DOCUMENTS

| | | |
|---|---|---|
| WO | WO-2000/16822 A1 | 3/2000 |
| WO | WO-2000/47114 A1 | 8/2000 |
| WO | WO-2002/040630 A2 | 5/2002 |
| WO | WO-2003/017826 A2 | 3/2003 |
| WO | WO-2003/032735 A1 | 4/2003 |
| WO | WO-2005/009134 A1 | 2/2005 |
| WO | WO-2007/043513 A1 | 4/2007 |
| WO | WO-2007/134134 A2 | 11/2007 |
| WO | WO-2009/009620 A2 | 1/2009 |
| WO | WO-2009/055610 A1 | 4/2009 |
| WO | WO-2010/019753 A2 | 2/2010 |
| WO | WO-2010/078353 A2 | 7/2010 |
| WO | WO-2011/019822 A2 | 2/2011 |
| WO | WO-2011/087743 A2 | 7/2011 |
| WO | WO-2012/019103 A2 | 2/2012 |
| WO | WO-2012/083412 A1 | 6/2012 |
| WO | WO-2012/109603 A1 | 8/2012 |
| WO | WO-2012/139593 A2 | 10/2012 |
| WO | WO-2012/142419 A1 | 10/2012 |
| WO | WO-2012/166784 A1 | 12/2012 |

OTHER PUBLICATIONS

Aycock et al., "Parastomal Hernia Repair With Acellular Dermal Matrix" *J. Wound Ostomy Continence Nurs.*, 34(5):521-523 (2007).

Badylak et al., "Endothelial cell adherence to small intestinal submucosa: An acellular bioscaffold" *Biomaterials*, 20:2257-2263 (1999).

Badylak et al., "Extracellular Matrix as a Biological Scaffold Material: Structure and Function" *Acta Biomaterialia*, 5(1):1-13 (2009).

Beniker et al., "The use of acellular dermal matrix as a scaffold for periosteum replacement" *Orthopedics*, 26(5 Suppl):s591-s596 (May 2003).

Bruder et al., "The Effect of Implants Loaded with Autologous Mesenchymal Stem Cells on the Healing of Canine Segmental Bone Defects" *J. Bone Joint Surg.*, 80:985-986 (1998).

Buma et al., "Tissue engineering of the meniscus" *Biomaterials*, 25(9):1523-1532 (2004).

(56) References Cited

OTHER PUBLICATIONS

Chaplin et al., "Use of an Acellular Dermal Allograft for Dural Replacement: An Experimental Study" *Neurosurgery*, 45(2):320-327 (Aug. 1999).
Chen et al. "Acellular Collagen Matrix as a Possible 'Off the Shelf' Biomaterial for Urethral Repair" *Urology*, 54(3):407-410 (1999).
Collins et al., "Cardiac xenografts between primate species provide evidence for the importance of the α-galactosyl determinant in hyperacute rejection" *J. Immunol.*, 154:5500-5510 (1995).
Costantino et al., "Human Dural Replacement With Acellular Dermis: Clinical Results and a Review of the Literature" *Head & Neck*, 22:765-771 (Dec. 2000).
Dobrin et al., "Elastase, collagenase, and the biaxial elastic properties of dog carotid artery" *Am. J. Physiol. Heart Circ. Physiol.*, 247:H124-H131 (1984).
Edel, "The use of a connective tissue graft for closure over an immediate implant covered with occlusive membrane" *Clin. Oral Implants Res.*, 6:60-65 (1995) (Abstract).
Fowler et al., "Ridge Preservation Utilizing an Acellular Dermal Allograft and Demineralized Freeze-Dried Bone Allograft: Part II. Immediate Endosseous Impact Placement" *J. Periodontol.*, 71:1360-1364 (2000).
Fowler et al., "Root Coverage with an Acellular Dermal Allograft: A Three-Month Case Report" *J. Contemp. Dental Pract.*, 1(3):1-8 (2000).
Galili et al., "Man, Apes, and Old World Monkeys Differ from Other Mammals in the Expression of α-Galactosyl Epitopes on Nucleated Cells" *J. Biol. Chem.*, 263(33):17755-17762 (1988).
Galili et al., "Interaction Between Human Natural Anti-α-Galactosyl Immunoglobulin G and Bacteria of the Human Flora" *Infect. Immun.*, 56(7):1730-1737 (1988).
Galili et al., "Interaction of the Natural Anti-Gal Antibody with α-Galactosyl Epitopes: a Major Obstacle for Xenotransplantation in Humans" *Immunology Today*, 14(10):480-482 (1993).
Gamba et al. "Experimental abdominal wall defect repaired with acellular matrix" *Pediatr. Surg. Int.*, 18:327-331 (2002).
Gebhart et al., "A radiographical and biomechanical study of demineralized bone matrix implanted into a bone defect of rat femurs with and without bone marrow" *Acta Orthop. Belg.*, 57(2):130-143 (1991) (Abstract).
Hammond et al., "Parastomal Hernia Prevention Using a Novel Collagen Implant: A Randomised Controlled Phase 1 Study" *Hernia*, 12:475-481 (2008).
Kish et al., "Acellular Dermal Matrix (AlloDerm): New Material in the Repair of Stoma Site Hernias" *The American Surgeon*, 71:1047-1050 (Dec. 2005).
Kridel et al., "Septal Perforation Repair with Acellular Human Dermal Allograft" *Arch. Otolaryngol. Head Neck Surg.*, 124:73-78 (Jan. 1998).
Laidlaw et al., "Tympanic Membrane Repair With a Dermal Allograft" *Laryngoscope*, 111:702-707 (Apr. 2001).
Lee et al., "In vitro evaluation of a poly(lactide-co-glycolide)-collagen composite scaffold for bone regeneration" *Biomaterials*, 27:3466-3472 (2006).
Lu et al., "Novel Porous Aortic Elastin and Collagen Scaffolds for Tissue Engineering" *Biomaterials*, 25(22):5227-5237 (2004).
Simon et al., "Early failure of the tissue engineered porcine heart valve SYNERGRAFT™ in pediatric patients" *Eur. J. Cardiothorac. Surg.*, 23(6):1002-1006 (2003).
Zheng et al. "Porcine small intestine submucosa (SIS) is not an acellular collagenous matrix and contains porcine DNA: Possible implications in human implantation" *J. Biomed. Mater. Res. B: Appl. Biomater.*, 73(1):61-67 (2005).
Duncan et al.; "Injectable Therapies for Localized Fat Loss: State of the Art;" Clin. Plastic Surg.; 38:489-501 (2011).
Smith et al.; "Autologous Human Fat Grafting: Effect of Harvesting and Preparation Techniques on Adipocyte Graft Survival;" Plastic and Reconstructive Surgery; 117(6):1836-1844 (2006).

Argenta, L.C. et al. "Vacuum-Assisted Closure: A New Method for Wound Control and Treatment: Clinical Experience" *Annals of Plastic Surgery*, 38(6):563-577 (Jun. 1997).
Blackburn II, J.H. et al. "Negative-Pressure Dressings as a Bolster for Skin Grafts" Annals of Plastic Surgery, 40(5):453-457 (May 1998).
Brandi, C. et al. "Treatment with vacuum-assisted closure and cryo-preserved homologous de-epidermalised dermis of complex traumas to the lower limbs with loss of substance, and bones and tendons exposure" *Journal of Plastic, Reconstructive and Aesthetic Surgery*, 61(12):1507-1511 (2008).
Chariker, M.E. et al. "Effective management of incisional and cutaneous fistulae with closed suction wound drainage" Contemporary Surgery, 34:59-63 (Jun. 1989).
Chinn, S.D. et al. "Closed Wound Suction Drainage" *The Journal of Foot Surgery*, 24(1):76-81 (1985).
Choi et al.; "Decellularized extracellular matrix derived from human adipose tissue as a potential scaffold for allograft tissue engineering"; J. Biomed. Mater Res. Part A; 97A(3):292-299 (2011).
Choi et al.; "Fabrication of Porous Extracellular Matrix Scaffolds from Human Adipose Tissue"; Tissue Engineering, Part C; 16(3):387-397 (2010).
Coleman et al.; "Fat Grafting to the Breast Revisited: Safety and Efficacy;" Plastic and Reconstructive Surgery; 119(3):775-785 (Mar. 2007).
Crapo et al.; "An overview of tissue and whole grain decellularization process;" Biomaterials; 32(12): 3233-3243 (Apr. 2011).
Dagalakis, N. et al. "Design of an artificial skin. Part III. Control of pore structure" *J. Biomed. Mater. Res.*, 14:511-528 (1980).
Dattilo Jr., P.P. et al. "Medical Textiles: Application of an Absorbable Barbed Bi-directional Surgical Suture" *Journal of Textile and Apparel, Technology and Management*, 2(2):1-5 (Spring 2002).
Defranzo, AJ. et al. "Vacuum-Assisted Closure for the Treatment of Abdominal Wounds" *Clinics in Plastic Surgery*, 33(2):213-224 (Apr. 2006).
Delay et al.; "Fat Injection to the Breast: Technique, Results and Indications Based on 880 Procedures Over 10 Years;" Aesthetic Surgery Journal; 29(5):360-376 (Sep./Oct. 2009).
Flack, S. et al. "An economic evaluation of VAC therapy compared with wound dressings in the treatment of diabetic foot ulcers" J. Wound Care, 17(2):71-78 (Feb. 2008).
Griffey, S. et al. "Particulate Dermal Matrix as an Injectable Soft Tissue Replacement Material" *J. Biomed. Mater. Res. (Appl. Biomater.)*, 58:10-15 (2001).
Ju, Y.M. et al., "Beneficial Effect of Hydrophilized Porous Polymer Scaffolds in Tissue-Engineered Cartilage Formation" *J. Biomed. Mater. Res. Part B: Appl. Biomater.*, 85B:252-260 (2008; online Oct. 31, 2007).
KCI Licensing, Inc. "VAC.® Therapy Safety Information" 2007, pp. 1-4.
Masters, J. "Reliable, Inexpensive and Simple Suction Dressings" Letters to the Editor, *British Journal of Plastic Surgery*, 51 (3):267 (1998).
O'Connor, J. et al. "Vacuum-Assisted Closure for the Treatment of Complex Chest Wounds" Ann. Thorac. Surg., 79:1196-1200 (2005).
O'Brien, F.J. et al., "The effect of pore size on cell adhesion in collagen-GAG scaffolds" *Biomaterials*, 26:433-441 (2005).
Pakhomov et al.; "Hydraulically Coupled Microejection Technique for Precise Local Solution Delivery in Tissues;" J. Neurosci Methods; 155(2):231-240 [Abstract] (Sep. 15, 2006).
Randall, K.L. et al. "Use of an Acellular Regenerative Tissue Matrix in Combination with Vacuum-assisted Closure Therapy for Treatment of a Diabetic Foot Wound" Journal of Foot and Ankle Surgery, 47(5):430-433 (2008).
Ting et al.; "A New Technique to Assist Epidural Needle Placement;" Anesthesiology; 112(5):1128-1135 (May 2010).
Wei, H-J. et al. "Construction of varying porous structures in acellular bovine pericardia as a tissue-engineering extracellular matrix" *Biomateria/s*, 26(14):1905-1913 (2005; online Jul. 17, 2004).
Wu et al.; An Injectable Adipose Matrix for Soft Tissue Reconstruction; Plastic and Reconstructive Surgery Advance Online Article; pp. 1-33 (2012).

(56) References Cited

OTHER PUBLICATIONS

Wu, Z. et al. "Preparation of collagen-based materials for wound dressing" *Chinese Medical Journal*, 116(3):419-423 (2003).

Xu, H. et al. "A Porcine-Derived Acellular Dermal Scaffold that Supports Soft Tissue Regeneration: Removal of Terminal Galactose-α-(1,3)-Galactose and Retention of Matrix Structure" Tissue Engineering, 15:1-13 (2009).

Yang, Q. et al. "A cartilage ECM-derived 3-D porous acellular matrix scaffold for in vivo cartilage tissue engineering with PKH26-labeled chondrogenic bone marrow-derived mesenchymal stem cells" *Biomaterials*, 29(15):2378-2387 (Mar. 4, 2008).

Yoshimura et al.; "Cell-Assisted Lipotransfer for Cosmetic Breast Augmentation: Supportive Use of Adipose-derived Stem/Stromal Cells;" Aesthetic Plastic Surgery Journal; 32:48-55 (2008).

\* cited by examiner

METHODS FOR IMPROVED TREATMENT OF ADIPOSE TISSUE

This application claims priority of U.S. Provisional Application No. 61/671,443, filed Jul. 13, 2012, which is incorporated herein by reference in its entirety.

BACKGROUND

The present disclosure relates generally to methods of treating tissue, and more specifically to methods of treating adipose tissue prior to implantation.

Autologous fat transfer is a process that can be used for cosmetic and reconstructive procedures. During autologous fat transfer, adipose tissue is harvested from one portion of a patient's body and is reimplanted in a different anatomic site. Generally, the harvested tissue is processed before reimplantation to remove undesirable substances such as pharmaceuticals introduced into the tissue during harvesting, and/or to increase the concentration of viable cells by removing excess fluids and non-viable materials such as extracellular matrix proteins and blood.

In the past, physicians have used various processing conditions in an attempt to improve the quality of adipose tissues for reimplantation. For example, poloxamers have been used in an attempt to stabilize or alter adipocyte cell membranes. Such approaches, however, may be overly complicated or expensive.

Current methods for processing adipose tissue for autologous fat transfer are effective but may be improved to provide higher-quality tissue for reimplantation. Accordingly, the present disclosure provides improved methods for processing tissue for autologous fat transfer.

According to certain embodiments, a method of treating tissue is provided. The method can comprise selecting a tissue comprising adipocytes for implantation; contacting the tissue with a detergent at a concentration and time sufficient to remove non-viable materials from the tissue; and rinsing the tissue to remove the detergent.

In addition, according to certain embodiments, tissue compositions comprising adipocyte-containing tissues prepared according to the disclosed methods are also provided. Also provided are methods of treatment comprising harvesting adipose tissue, processing the tissue according to any of the disclosed methods, and reimplanting the tissue into a patient.

DESCRIPTION OF EXEMPLARY EMBODIMENTS

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. Also in this application, the use of "or" means "and/or" unless stated otherwise. Furthermore, the use of the term "including," as well as other forms, such as "includes" and "included," are not limiting. Any range described herein will be understood to include the endpoints and all values between the end points.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Autologous fat transfer is a procedure that involves harvesting a patient's adipose tissue for implantation elsewhere in the patient's body. Adipose tissue grafting involves a number of steps, which can include: collecting, processing, and/or implantation of the tissue.

Harvested adipose tissue, as may be used for fat transfer, may contain substances that can adversely affect the viability of adipose cells after implantation. For example, harvested adipose tissue may contain Ringer's lactate solution, epinephrine, blood, and free lipids, as well as particulates including extracellular matrix. Some of these substances, including blood, free lipids and collagen, can incite an inflammatory response that may adversely impact the ability of the adipose tissue to successfully integrate upon implantation.

Moreover, in some cases, it is desirable to control the number of adipocytes per unit volume of tissue to be implanted. For example, certain substances such as water, blood, and extracellular matrix proteins may be reabsorbed or broken down by the body after implantation. Accordingly, the volume of tissue that is implanted can decrease significantly after implantation, thereby inadequately filling an implantation site. It may, therefore, be desirable to remove certain amounts of water, blood, proteins, and/or materials other than adipocytes in order to increase the concentration of adipocytes per unit volume of tissue prior to reimplantation.

Harvested adipose tissue is often washed with crystalloid solutions such as sterile saline solutions or Ringer's lactate to decrease the amount of non-viable materials or contaminants in the adipose tissue. Washing with such solutions, however, may not remove sufficient amounts of non-viable materials or contaminants. The present disclosure provides enhanced methods of treatment of harvested tissue to improve tissue viability after implantation. In certain embodiments, the present disclosure provides an improved method to wash harvested tissue to remove substances that may adversely affect a tissue graft after implantation. Further, washing the tissue according to the methods of the present disclosure can result in an increased concentration of viable adipocytes per unit of tissue. In certain embodiments, the tissue is prepared such that the number of viable adipocytes per volume of tissue is at least two times the number of viable adipocytes per volume of tissue in unprocessed human adipose tissue.

In various embodiments, the methods of the present disclosure provide more effective washing, which results in increased removal rates of deleterious or non-viable substances compared to washing with saline or Ringer's lactate solutions. In one embodiment, the tissue treated according to the methods of the present disclosure has an increased likelihood of remaining viable after implantation. Furthermore, after rinsing, water may be removed from the tissue by drying, suction, compression, or other suitable means in order to increase the concentration of adipocytes prior to implantation.

In various embodiments, the methods include washing tissue with biocompatible detergents. In various embodiments, the detergent is a nonionic detergent. In certain embodiments, the detergent may also be referred to as a washing agent or surfactant. Detergents may include commercially sold detergents, as well a solutions prepared by the dilution of commercially available detergents. Detergents useful in the present disclosure are nontoxic, medical grade, and/or biocompatible detergents.

In certain embodiments, the detergents are approved for human and veterinary use. In various embodiments, the detergents meet the standards of the United States Pharmacopoeia (USP), the European Pharmacopoeia (EP), the British Pharmacopoeia, and/or the International Pharmacopoeia. In certain embodiments, the detergents meet the standards of the United States Pharmacopoeia and the National Formulary (USP-NF). Non-exclusive examples of detergents useful in the methods of the present disclosure include TWEEN and TRITON-X. In certain embodiments, the detergent can include common soaps formed of synthetic surfactants and/or animal derived surfactants (e.g., tallow). In some embodiments, the detergent comprises a biocompatible detergent. In some embodiments, the detergent comprises a surfactant that is not a poloxamer.

Washing of adipose tissue may be carried using a variety of techniques and processing conditions. In certain embodiments, the removal of non-viable material from the harvested tissue may be further enhanced by maximization of the tissue surface brought into contact with the detergent. In certain embodiments, enhanced surface contact is achieved by agitating the tissue and/or the washing solution. Agitation can include mechanical stirring, shaking, and/or pressurized application of washing fluid to achieve a fluidized bed-like behavior.

In some embodiments, the detergent and non-viable materials are removed from the tissue by rinsing prior to implantation. In some embodiments, the tissue is rinsed with sterile saline. In some embodiments, the washed tissue is rinsed more than once until desired removal of the detergent and/or non-viable materials is achieved.

The methods of the present disclosure can be performed under conditions sufficient to effectively remove non-viable materials that may lead to undesirable tissue inflammation. The methods of the present disclosure are also directed to the removal of non-viable material, such that the number of viable adipocytes per volume of tissue is greater than the number of viable adipocytes per volume of tissue in unprocessed human adipose tissue. In one embodiment, the methods of the present disclosure are used to prepare tissue such that the number of viable adipocytes per volume of tissue is at least two times the number of viable adipocytes per volume of tissue in unprocessed human adipose tissue.

The methods of the present disclosure can be performed using a variety of different devices and/or systems. For example, washing according to the methods of the present disclosure can be performed using any suitable container such as a liposuction collection system, a bag, or other biocompatible container. In addition, specialized washing systems may be used. For example, a suitable device for collecting, washing, and/or processing adipose tissue is discussed in U.S. Provisional Patent Application No. 61/653,011, which was filed on May 20, 2012, and is titled "Device for Harvesting, Processing, and Transferring Adipose Tissue."

In various embodiments, tissue compositions are also provided. The tissue compositions can comprise adipocyte-containing tissues prepared according to any of the foregoing methods. In some embodiments, tissue compositions comprise adipose tissue, and the tissue is prepared such that the number of viable adipocytes per volume of tissue is greater than the number of viable adipocytes per volume of tissue in unprocessed human adipose tissue. In other embodiments, the tissue is prepared such that the number of viable adipocytes per volume of tissue is at least two times the number of viable adipocytes per volume of tissue in unprocessed human adipose tissue.

Also provided are methods of treatment using tissues prepared according to any of the forgoing methods. In certain embodiments, the methods comprise harvesting adipose tissue, treating the tissue according to any of the methods described herein, and implanting the tissue.

It will be appreciated that, although the exemplary methods described herein are suitable for processing of tissue for autologous fat transfer, the methods can be used for other types of fat transfer, including allogeneic and xenogeneic procedures.

It will be readily apparent to one of ordinary skill in the relevant arts that other suitable modifications and adaptations to the methods and applications described herein are suitable and may be made without departing from the scope of the invention or any embodiment thereof. While the invention has been described in connection with certain embodiments, it is not intended to limit the invention to the particular forms set forth, but on the contrary, it is intended to cover such alternatives, modifications and equivalents as may be included within the spirit and scope of the invention as defined by the following claims.

What is claimed is:

1. A method for treating tissue comprising:
   selecting a tissue comprising adipocytes for implantation;
   contacting the tissue with a detergent at a concentration and time sufficient to remove non-viable materials comprising blood, water, and particulate tissue matrix from the tissue to produce an adipose tissue comprising adipocytes and adipose extracellular tissue matrix, wherein a poloxamer is not used in the contacting step; and
   rinsing the tissue to remove the detergent, such that the contacting and rinsing increase the concentration of viable adipocytes in the tissue as compared to the tissue prior to treatment.

2. The method according to claim 1, wherein the method is performed prior to implantation of the tissue during autologous fat transfer.

3. The method according to claim 1, wherein the detergent is a nonionic detergent.

4. The method according to claim 1, wherein the detergent is a biocompatible detergent.

5. The method according to claim 1, wherein the detergent comprises a polysorbate.

6. The method according to claim 1, wherein the detergent comprises a polyethylene glycol.

7. The method according to claim 1, wherein the non-viable materials further comprise pharmaceutical agents and epinephrine.

8. The method according to claim 1, wherein the tissue is contacted with the detergent and rinsed under conditions selected to reduce the water content of the tissue.

9. The method according to claim 1, further comprising agitating the tissue while the tissue is in contact with the detergent.

10. The method of claim 9, wherein agitating the tissue comprises at least one of stirring, shaking, and causing the detergent to flow in contact with the tissue.

11. The method according to claim 1, further comprising repeating the steps of contacting the tissue with the detergent and rinsing the tissue.

12. The method according to claim 1, wherein the tissue is rinsed with a rinsing fluid comprising a saline solution.

13. The method according to claim 1, further comprising implanting the tissue in a patient.

14. The method according to claim 1, further comprising removing water from the tissue.

15. The method according to claim 1, wherein the contacting and rinsing at least doubles the concentration of viable adipocytes in the tissue as compared to the tissue prior to treatment.

* * * * *

UNITED STATES PATENT AND TRADEMARK OFFICE
CERTIFICATE OF CORRECTION

PATENT NO. : 11,090,338 B2  
APPLICATION NO. : 13/929252  
DATED : August 17, 2021  
INVENTOR(S) : Aaron Barere et al.

Page 1 of 1

It is certified that error appears in the above-identified patent and that said Letters Patent is hereby corrected as shown below:

In the Claims

In Claim 5 (Column 4, Line 45), please replace "according claim 1," with -- according to claim 1, --

Signed and Sealed this  
Nineteenth Day of October, 2021

Drew Hirshfeld  
*Performing the Functions and Duties of the*  
*Under Secretary of Commerce for Intellectual Property and*  
*Director of the United States Patent and Trademark Office*